(12) United States Patent
Chau et al.

(10) Patent No.: US 8,753,373 B2
(45) Date of Patent: Jun. 17, 2014

(54) SUTURE-FASTENING CLIP

(75) Inventors: Mark Chau, Somis, CA (US); Kevin Golemo, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1613 days.

(21) Appl. No.: 11/746,009

(22) Filed: May 8, 2007

(65) Prior Publication Data
US 2008/0281356 A1   Nov. 13, 2008

(51) Int. Cl.
   *A61B 17/04*   (2006.01)

(52) U.S. Cl.
   USPC .................. 606/232; 606/144; 606/151

(58) Field of Classification Search
   USPC .......................... 606/232, 144, 148
   See application file for complete search history.

(56) References Cited

U.S. PATENT DOCUMENTS

| | | | |
|---|---|---|---|
| 3,769,980 A | 11/1973 | Karman | |
| 3,805,793 A | 4/1974 | Wright | |
| 4,055,167 A | 10/1977 | Bernstein | |
| 4,274,324 A * | 6/1981 | Giannuzzi | 411/38 |
| 4,311,140 A | 1/1982 | Bridgman | |
| 4,350,160 A | 9/1982 | Kolesov et al. | |
| 5,080,663 A | 1/1992 | Mills et al. | |
| 5,242,456 A | 9/1993 | Nash et al. | |
| 5,267,958 A | 12/1993 | Buckbinder et al. | |
| 5,330,442 A | 7/1994 | Green et al. | |
| 5,374,275 A | 12/1994 | Bradley et al. | |
| 5,403,326 A | 4/1995 | Harrison et al. | |
| 5,443,446 A | 8/1995 | Shturman | |
| 5,458,131 A | 10/1995 | Wilk | |
| 5,474,573 A | 12/1995 | Hatcher | |
| 5,534,012 A * | 7/1996 | Bonutti | 606/232 |
| 5,540,704 A | 7/1996 | Gordon et al. | |
| 5,569,274 A | 10/1996 | Rapacki et al. | |
| 5,573,540 A | 11/1996 | Yoon | |
| 5,575,800 A | 11/1996 | Gordon | |
| 5,578,044 A | 11/1996 | Gordon et al. | |
| 5,601,574 A | 2/1997 | Stefanchik et al. | |
| 5,609,598 A | 3/1997 | Laufer et al. | |
| 5,643,289 A | 7/1997 | Sauer et al. | |
| 5,645,589 A * | 7/1997 | Li | 606/60 |
| 5,662,664 A | 9/1997 | Gordon et al. | |
| 5,685,867 A | 11/1997 | Twardowski et al. | |
| 5,695,457 A | 12/1997 | St. Goar et al. | |

(Continued)

FOREIGN PATENT DOCUMENTS

DE   19725739   4/1999
EP   570915     11/1993

(Continued)

*Primary Examiner* — Corrine M McDermott
*Assistant Examiner* — Alexander Orkin
(74) *Attorney, Agent, or Firm* — David L. Hauser

(57) ABSTRACT

A clip for securing suture to tissue includes a generally tubular body, with at least one bend area along the length of the generally tubular body and one or more tabs cut from the wall of the generally tubular body. The clip in the open configuration is generally straight along the length of the generally tubular body, and the tabs are in general alignment with the tab out wall. The tab in a closed configuration assumes a shape having at least one bend along its length, and the tabs are bent or otherwise positioned to extend into and at least partially obstruct the inner lumen. The clip can be formed from memory material such as nitinol, and the clip may be biased toward its closed configuration.

18 Claims, 14 Drawing Sheets

(56) References Cited

U.S. PATENT DOCUMENTS

| | | | |
|---|---|---|---|
| 5,695,504 | A | 12/1997 | Gifford et al. |
| 5,700,272 | A | 12/1997 | Gordon et al. |
| 5,713,910 | A | 2/1998 | Gordon et al. |
| 5,713,911 | A | 2/1998 | Racenet et al. |
| 5,716,367 | A | 2/1998 | Koike et al. |
| 5,741,277 | A | 4/1998 | Gordon et al. |
| 5,741,279 | A | 4/1998 | Gordon et al. |
| 5,766,183 | A | 6/1998 | Sauer |
| 5,769,863 | A | 6/1998 | Garrison |
| 5,792,094 | A | 8/1998 | Stevens et al. |
| 5,792,153 | A | 8/1998 | Swain et al. |
| 5,810,847 | A | 9/1998 | Laufer et al. |
| 5,814,097 | A | 9/1998 | Sterman et al. |
| 5,836,956 | A | 11/1998 | Buelna et al. |
| 5,839,639 | A | 11/1998 | Sauer et al. |
| 5,840,030 | A | 11/1998 | Ferek-Petric et al. |
| 5,849,019 | A | 12/1998 | Yoon |
| 5,860,992 | A | 1/1999 | Daniel et al. |
| 5,885,238 | A | 3/1999 | Stevens et al. |
| 5,891,159 | A | 4/1999 | Sherman et al. |
| 5,891,160 | A | 4/1999 | Williamson et al. |
| 5,924,424 | A | 7/1999 | Stevens et al. |
| 5,928,224 | A | 7/1999 | Laufer |
| 5,928,250 | A | 7/1999 | Koike et al. |
| 5,968,059 | A | 10/1999 | Ellis et al. |
| 5,972,020 | A | 10/1999 | Carpentier et al. |
| 5,976,159 | A | 11/1999 | Bolduc et al. |
| 6,004,310 | A | 12/1999 | Bardsley et al. |
| 6,010,531 | A | 1/2000 | Donlon et al. |
| 6,015,417 | A | 1/2000 | Reynolds, Jr. |
| 6,015,427 | A | 1/2000 | Mueller et al. |
| 6,029,671 | A | 2/2000 | Stevens et al. |
| 6,047,700 | A | 4/2000 | Eggers et al. |
| 6,056,760 | A | 5/2000 | Koike et al. |
| 6,080,182 | A | 6/2000 | Shaw et al. |
| 6,083,219 | A | 7/2000 | Laufer |
| 6,088,889 | A | 7/2000 | Luther et al. |
| 6,117,159 | A | 9/2000 | Huebsch et al. |
| 6,136,010 | A | 10/2000 | Modesitt et al. |
| 6,149,660 | A | 11/2000 | Laufer et al. |
| 6,157,852 | A | 12/2000 | Selmon et al. |
| 6,162,233 | A | 12/2000 | Williamson et al. |
| 6,165,183 | A | 12/2000 | Kuehn et al. |
| 6,165,204 | A | 12/2000 | Levinson et al. |
| 6,190,357 | B1 | 2/2001 | Ferrari et al. |
| 6,210,419 | B1 | 4/2001 | Mayenberger et al. |
| 6,234,995 | B1 | 5/2001 | Peacock |
| 6,238,336 | B1 | 5/2001 | Ouchi |
| 6,269,819 | B1 | 8/2001 | Oz et al. |
| 6,312,447 | B1 | 11/2001 | Grimes |
| 6,443,922 | B1 | 9/2002 | Roberts et al. |
| 6,461,366 | B1 | 10/2002 | Seguin |
| 6,464,707 | B1 | 10/2002 | Bjerken et al. |
| 6,475,230 | B1 * | 11/2002 | Bonutti et al. ............ 606/232 |
| 6,508,777 | B1 | 1/2003 | Macoviak et al. |
| 6,551,330 | B1 | 4/2003 | Bain et al. |
| 6,575,971 | B2 | 6/2003 | Hauck et al. |
| 6,582,388 | B1 | 6/2003 | Coleman et al. |
| 6,626,930 | B1 | 9/2003 | Allen et al. |
| 6,629,534 | B1 | 10/2003 | St. Goar et al. |
| 6,638,293 | B1 | 10/2003 | Makower et al. |
| 6,641,592 | B1 | 11/2003 | Sauer et al. |
| 6,645,205 | B2 | 11/2003 | Ginn |
| 6,746,472 | B2 * | 6/2004 | Frazier et al. ............ 606/232 |
| 6,752,813 | B2 | 6/2004 | Goldfarb et al. |
| 6,770,083 | B2 | 8/2004 | Seguin |
| 6,860,890 | B2 | 3/2005 | Bachman et al. |
| 6,875,224 | B2 | 4/2005 | Grimes |
| 6,911,034 | B2 | 6/2005 | Nobles et al. |
| 6,997,931 | B2 | 2/2006 | Sauer et al. |
| 7,083,628 | B2 | 8/2006 | Bachman |
| 7,094,244 | B2 | 8/2006 | Schreck |
| 7,674,274 | B2 * | 3/2010 | Foerster et al. ............ 606/232 |
| 7,815,655 | B2 * | 10/2010 | Catanese et al. ............ 606/151 |
| 2002/0049402 | A1 | 4/2002 | Peacock et al. |
| 2002/0107530 | A1 | 8/2002 | Sauer et al. |
| 2002/0107531 | A1 | 8/2002 | Schreck et al. |
| 2003/0130571 | A1 | 7/2003 | Lattouf |
| 2003/0167062 | A1 | 9/2003 | Gambale et al. |
| 2003/0167071 | A1 | 9/2003 | Martin |
| 2003/0195524 | A1 | 10/2003 | Barner |
| 2003/0208209 | A1 | 11/2003 | Gambale |
| 2004/0044365 | A1 | 3/2004 | Bachman |
| 2004/0049215 | A1 | 3/2004 | Snow et al. |
| 2004/0068272 | A1 | 4/2004 | Sauer et al. |
| 2004/0181238 | A1 | 9/2004 | Zarbatany et al. |
| 2004/0204724 | A1 * | 10/2004 | Kissel et al. ............ 606/151 |
| 2005/0251209 | A1 * | 11/2005 | Saadat et al. ............ 606/232 |
| 2006/0004410 | A1 | 1/2006 | Nobis et al. |
| 2006/0167338 | A1 | 7/2006 | Schfaram |
| 2007/0010857 | A1 * | 1/2007 | Sugimoto et al. ............ 606/232 |
| 2007/0049970 | A1 * | 3/2007 | Belef et al. ............ 606/232 |
| 2007/0179530 | A1 * | 8/2007 | Tieu et al. ............ 606/232 |

FOREIGN PATENT DOCUMENTS

| | | |
|---|---|---|
| EP | 769272 | 4/1997 |
| EP | 861632 | 9/1998 |
| FR | 2768324 | 3/1999 |
| WO | WO 93/08738 | 5/1993 |
| WO | WO 95/15715 | 6/1995 |
| WO | WO 95/25468 | 9/1995 |
| WO | WO 97/13463 | 4/1997 |
| WO | WO 97/27807 | 8/1997 |
| WO | WO 97/27893 | 8/1997 |
| WO | WO 98/57585 | 12/1998 |
| WO | WO 99/00059 | 1/1999 |
| WO | WO 99/13777 | 3/1999 |
| WO | WO 99/15223 | 4/1999 |
| WO | WO 99/35980 | 7/1999 |
| WO | WO 00/03759 | 2/2000 |
| WO | WO 00/59382 | 10/2000 |
| WO | WO 00/60995 | 10/2000 |
| WO | WO 01/26557 | 4/2001 |
| WO | WO 01/28432 | 4/2001 |
| WO | WO 01/66018 | 9/2001 |
| WO | WO 01/95809 | 12/2001 |
| WO | WO 02/24078 | 3/2002 |
| WO | WO 02/34167 | 5/2002 |
| WO | WO 02/45598 | 6/2002 |
| WO | WO 03/001893 | 1/2003 |
| WO | WO 03/103536 | 12/2003 |
| WO | WO 2005/110244 | 11/2005 |

* cited by examiner

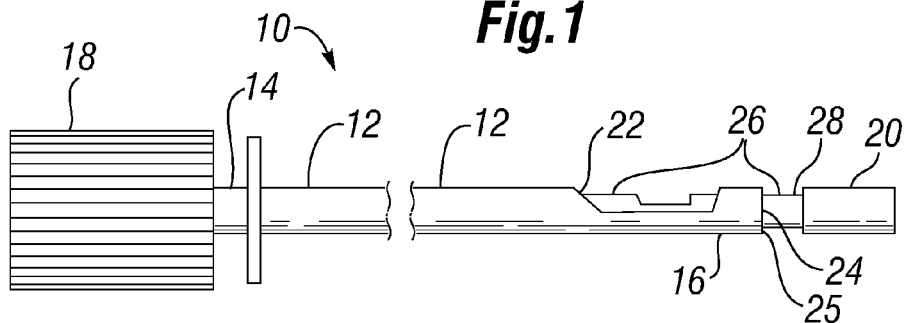
Fig.1
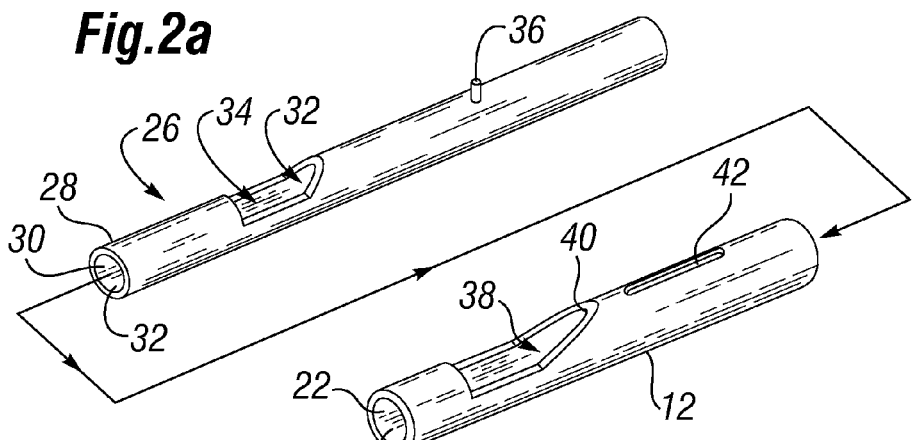
Fig.2a
Fig.2b
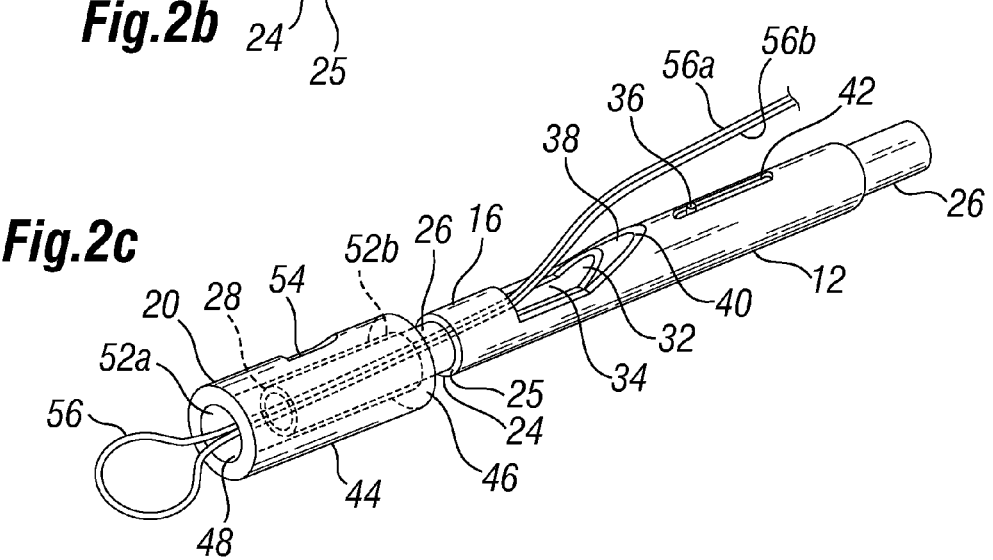
Fig.2c

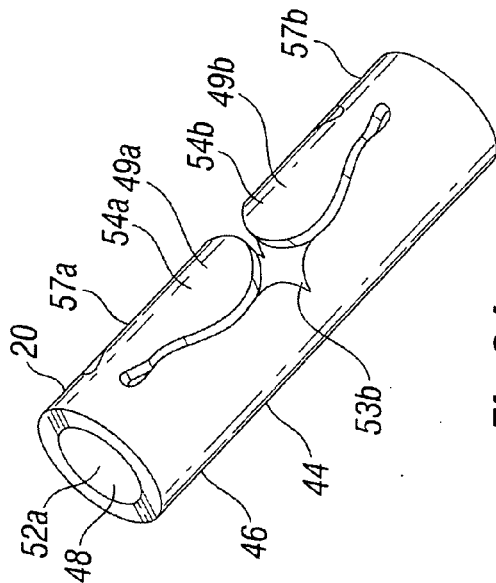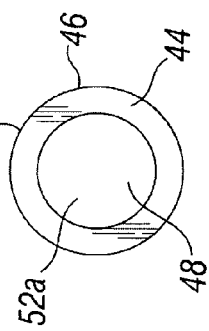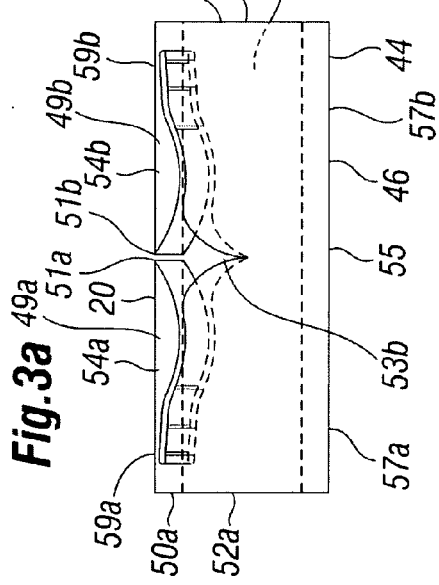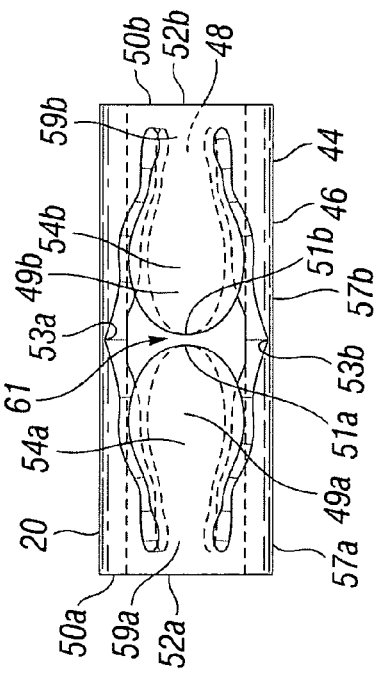

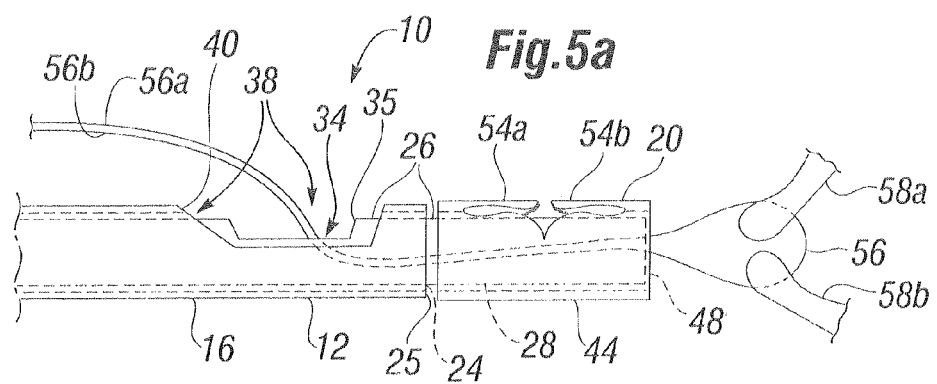
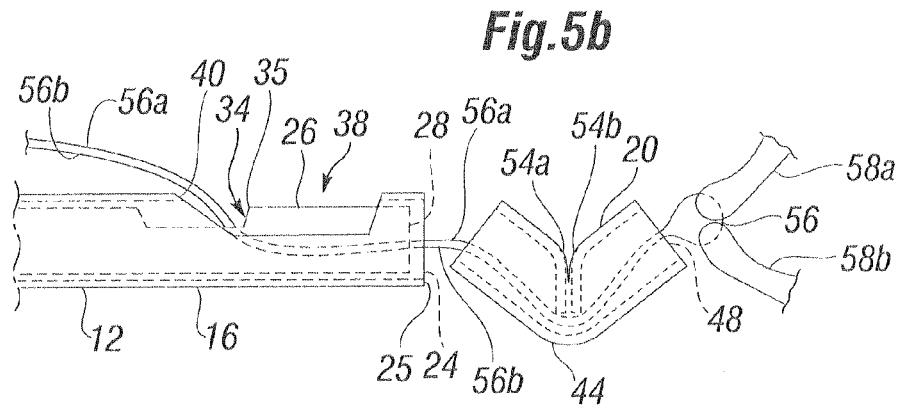
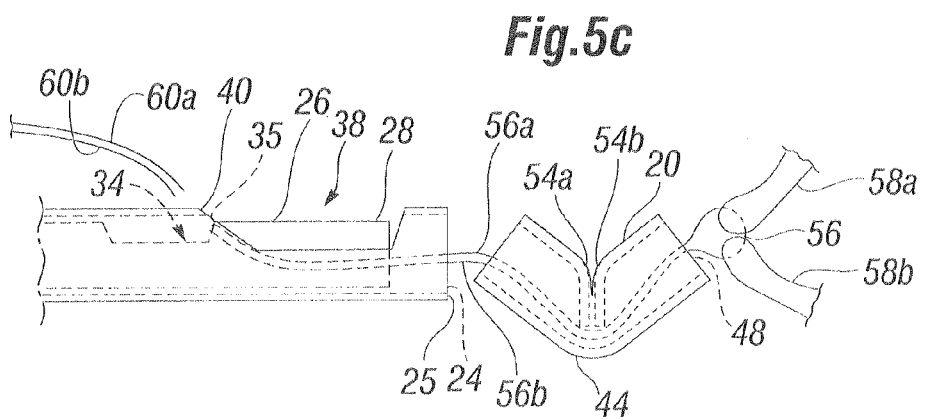

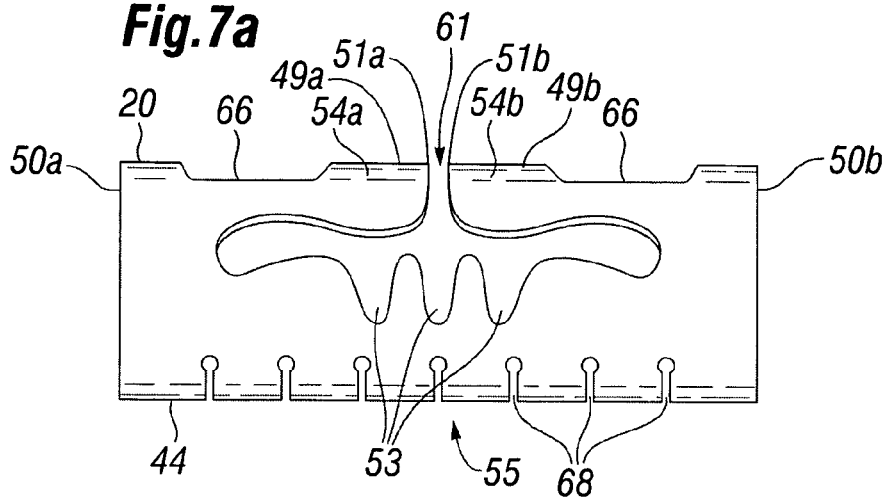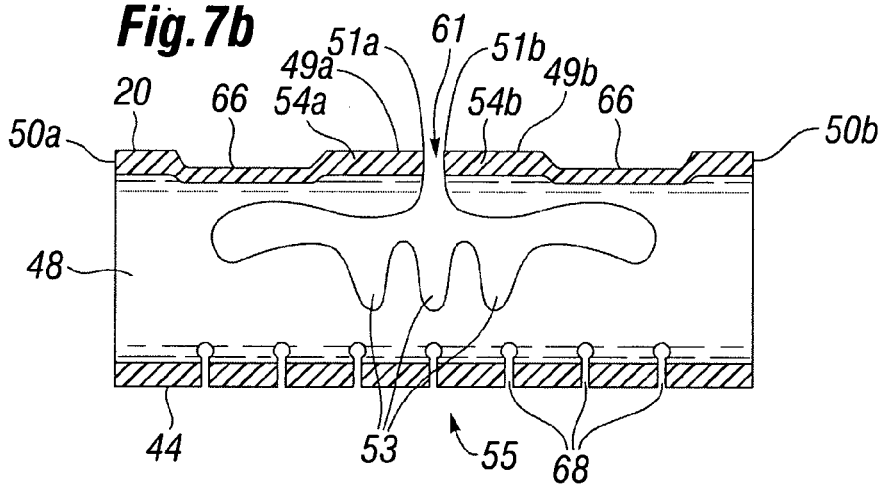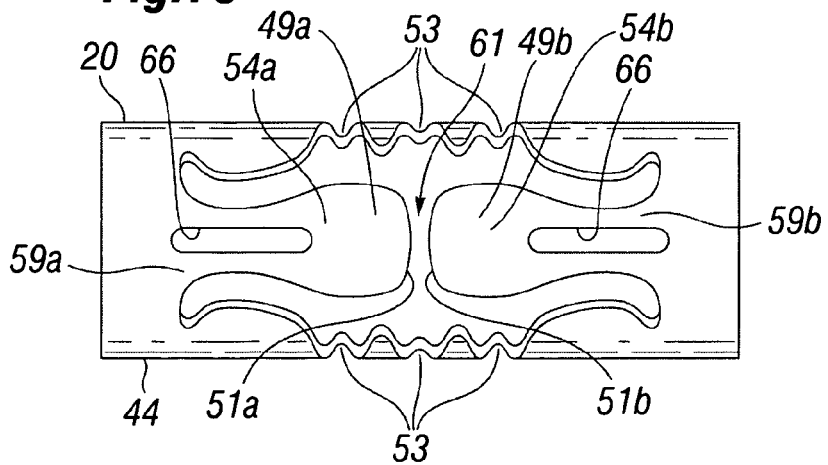

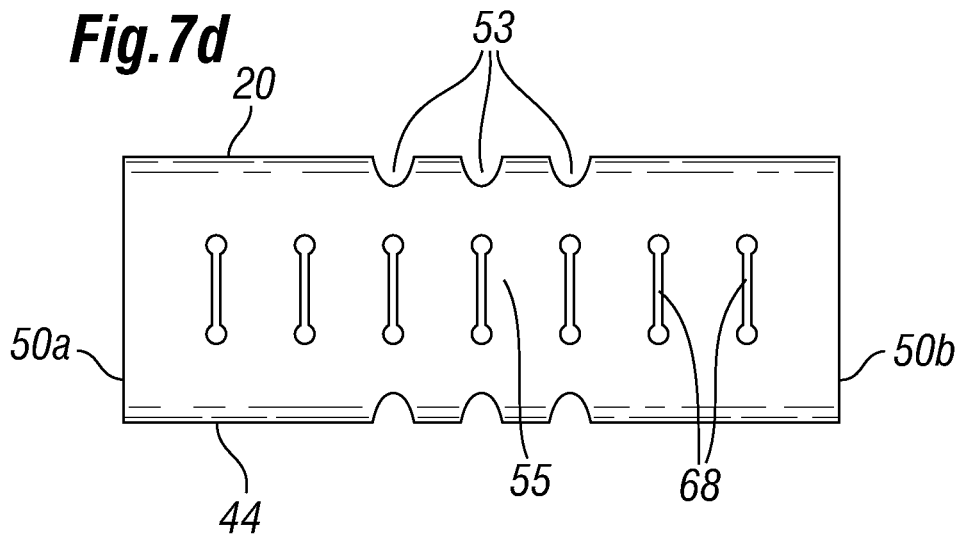
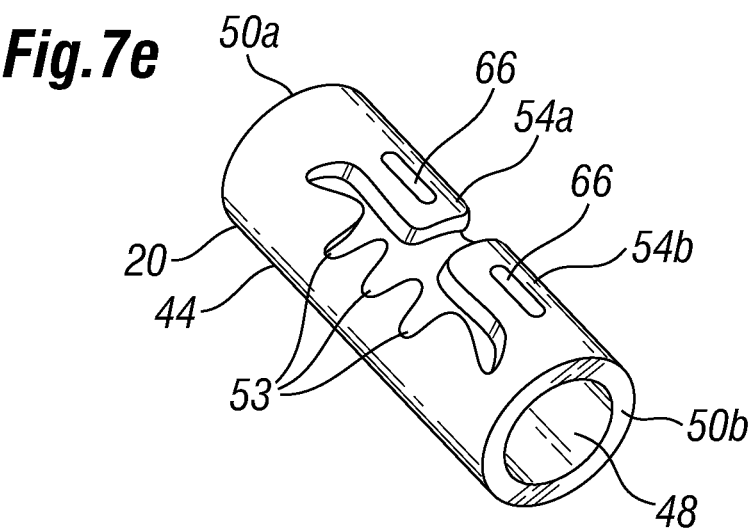
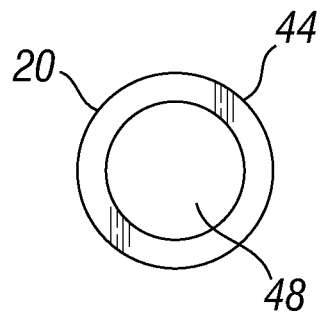

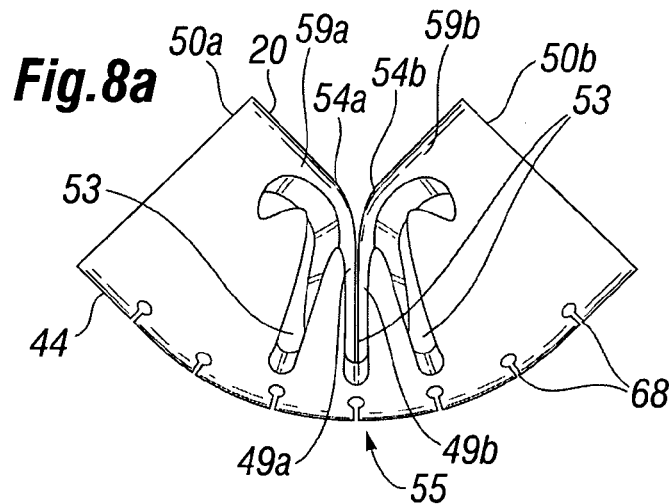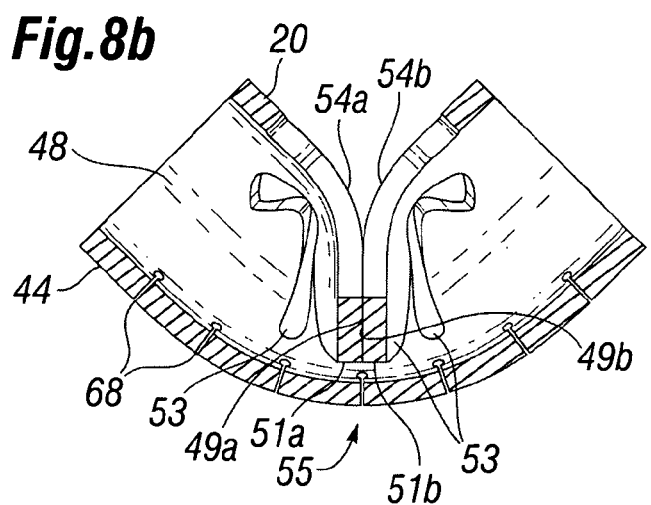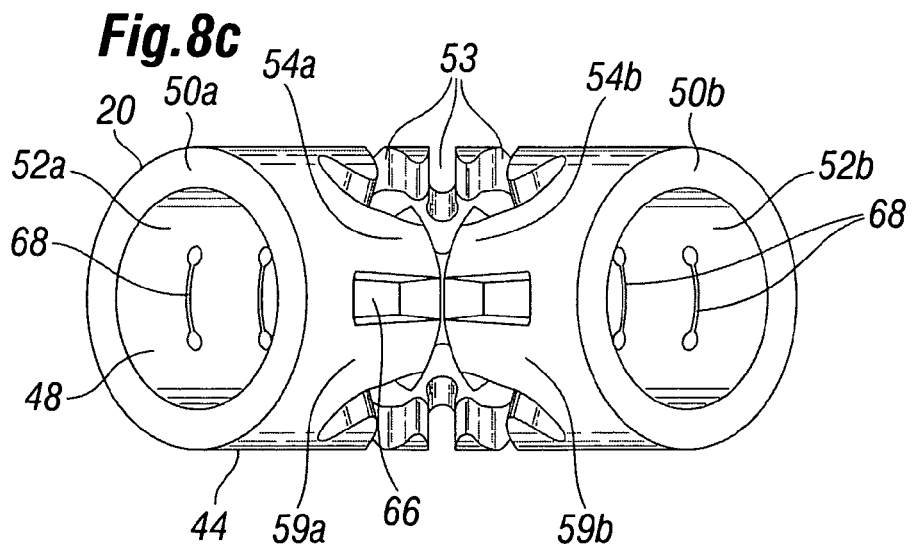

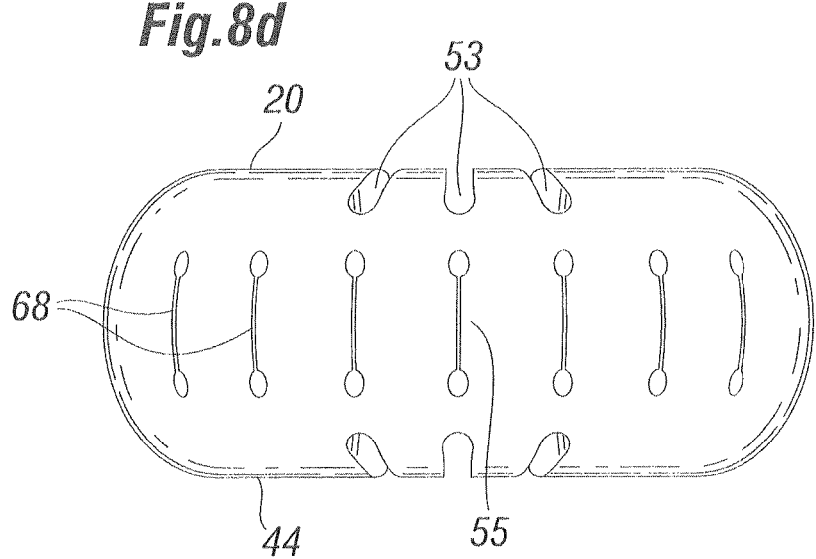
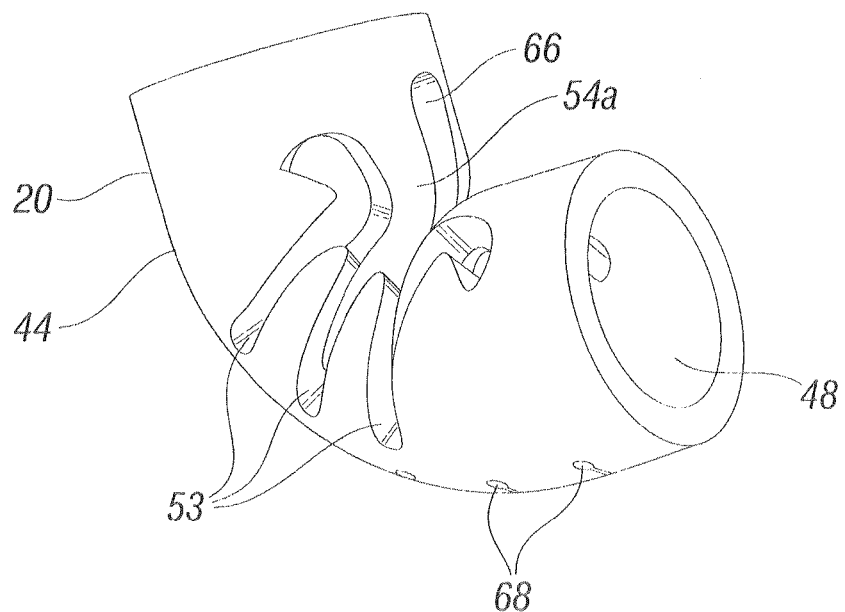

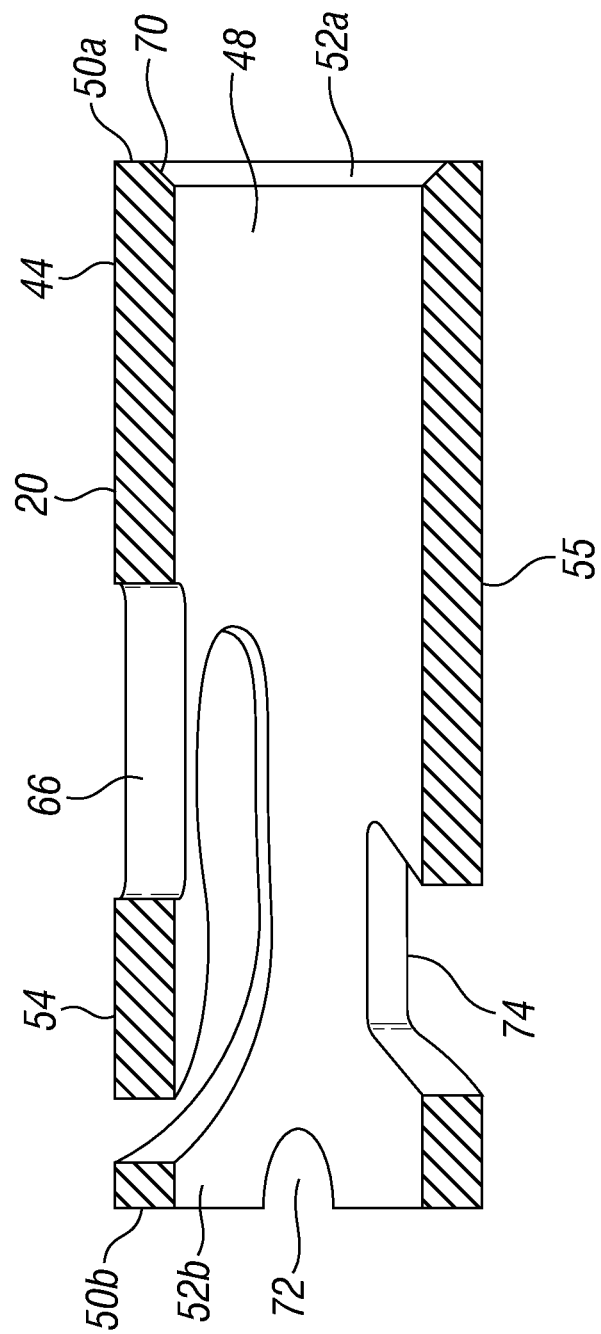

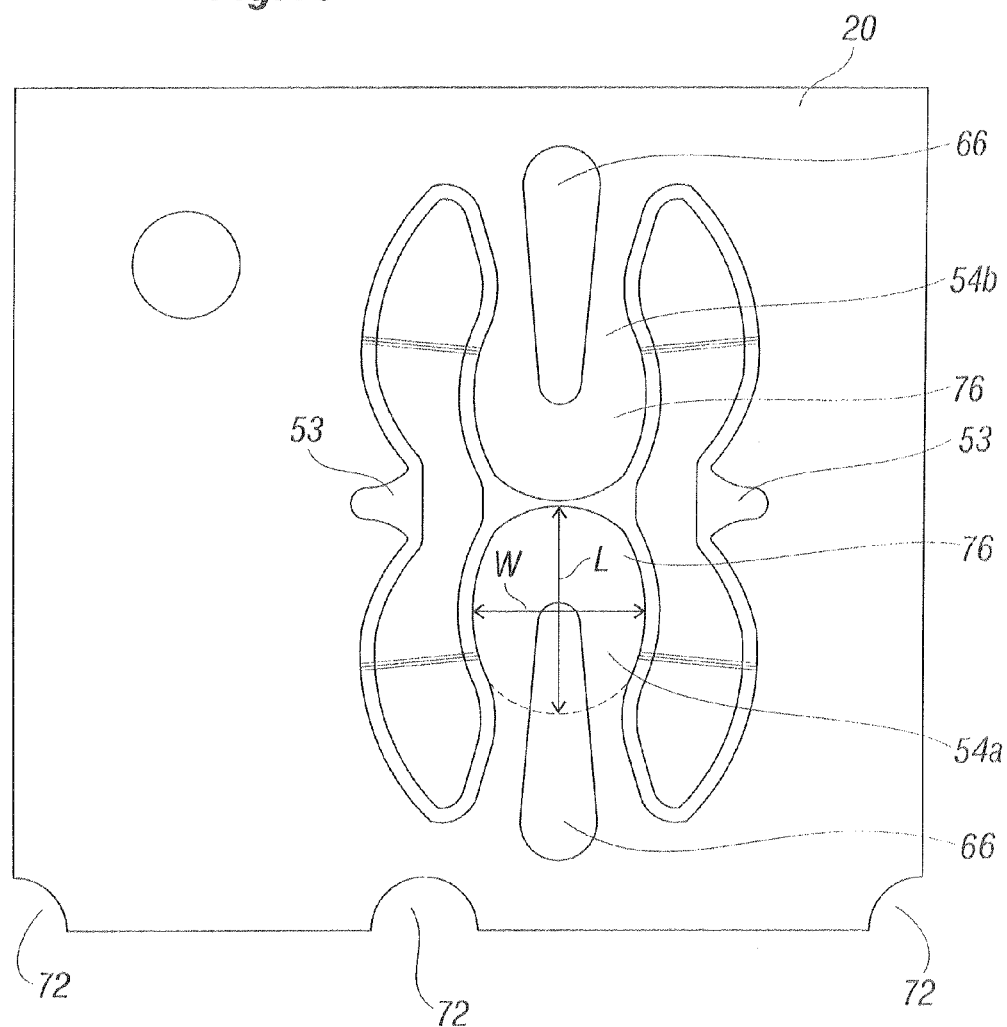

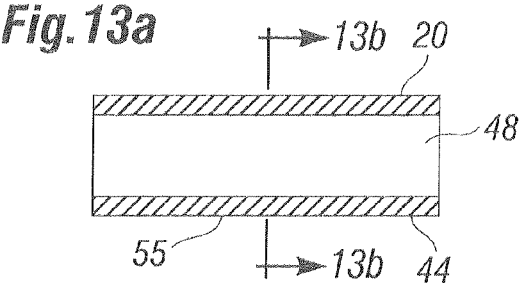
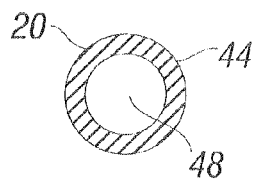
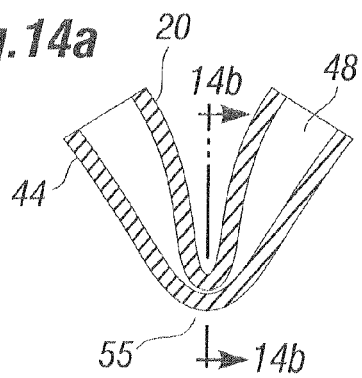
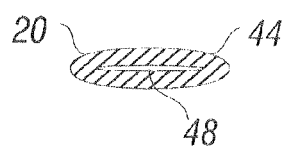
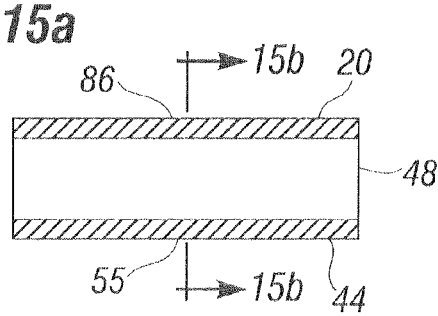
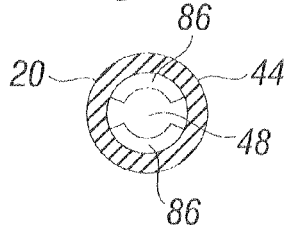
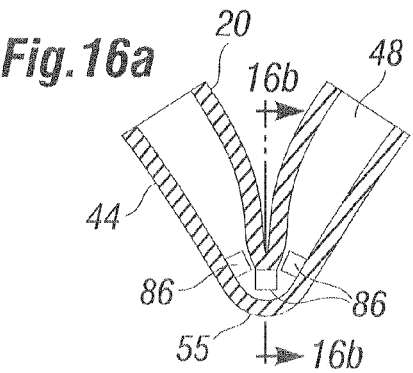
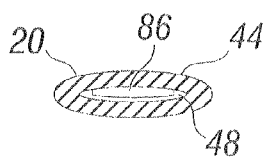

SUTURE-FASTENING CLIP

FIELD OF THE INVENTION

The present invention relates to medical devices and methods. In particular, the present invention relates to a system, apparatus, and method or joining tissue, and particularly for joining tissue using a suture and fastener clip.

BACKGROUND OF THE INVENTION

Many medical procedures involve joining tissue pieces. Joining adjacent tissue pieces is commonly performed using suture, particularly where the tissue pieces are easily accessible to the surgeon. In conventional surgical techniques, the surgeon will join the tissue pieces by forcing a needle and suture material through various portions of the tissue, and then tying a knot in the suture material to securely join the tissue pieces.

Minimally invasive surgical techniques have emerged as an alternative to conventional surgical techniques to perform a plurality of surgical procedures. Minimally invasive procedures differ from conventional surgical procedures in that a plurality of devices may be introduced into the body through a small incision. As a result, trauma to the body is greatly reduced, thereby decreasing the recovery time of the patient.

Percutaneous and other minimally-invasive methods of surgery, where the surgery may be performed remotely via catheters, often include the need to fasten tissue pieces which the surgeon cannot directly access. For example, in percutaneous operations to close a patent foramen ovale (PFO), adjacent tissue pieces on either side of the PFO must be joined together via a catheter. In so-called edge-to-edge valve repairs, adjacent valve leaflet edges are joined together to restore valve functionality. Further information on these and similar procedures for which the current invention can be applicable are disclosed in the following references, the entire contents of which are expressly incorporated herein by reference: U.S. Pat. No. 6,626,930 issued to Allen et al.; U.S. patent application Ser. No. 10/106,583, filed Mar. 26, 2002 and entitled, "Sequential Heart Valve Leaflet Repair Device and Method of Use"; U.S. patent application Ser. No. 10/233,879, filed Sep. 3, 2002 and entitled "Single Catheter Mitral Valve Repair Device and Method"; U.S. patent application Ser. No. 10/389,721, filed Mar. 14, 2003 and entitled "Mitral Valve Repair System and Method of Use"; and patent application Ser. No. 11/174,143, filed Jun. 30, 2005 and entitled "System, Apparatus, and Method for Repairing Septal Defects."

One challenge presented when performing a heretofore conventional surgical procedure using a minimally invasive technique is to remotely position and secure sutures to an area of interest. In minimally invasive surgical techniques the surgeon's access to the approximation site is greatly reduced. One method involves using a surgical device to attach the suture material to the tissue, while allowing for sufficient suture so that the suture ends lead outside of the patient's body for easy access by the surgeon. The surgeon can remotely form a loose knot in the suture material and advance the knot to the tissue within the patient using a so-called "knot pusher." The surgeon can then remotely tighten the suture and knot, thereby joining the tissue pieces together.

Several knot pushing devices are known which permit an operator to push suture knots which have been formed extracorporeally towards tissue to be sutured. For example, U.S. Pat. No. 5,769,863, issued to Garrison et al., discloses a surgical knot pusher having an elongated body connected to a pushing head. The pushing head engages a portion of suture material containing a knot and is advanced to the area of interest, thereby "throwing" the knot. Once the suture knot is placed the knot pushing device is removed and a cutting implement is introduced into the body and cuts the remaining suture material. The remaining suture material is then removed. Another example of a knot pusher is disclosed in U.S. Pat. No. 6,860,890, entitled "Surgical Knot Pushing Device and Method of Use," the entire contents of which are expressly incorporated herein by reference.

Another method of securing suture material involves using a clip to secure the suture together. The clip can be delivered remotely by advancing the clip along a relatively long suture line to the area of interest, and then deploying the clip such that the clip secures the suture in place. With the clip thus secured, the excess suture can be cut and removed from the patient. An example of such a clip as well as methods and devices for use therewith are disclosed in patent application Ser. No. 11/174,357 filed Jun. 30, 2005 and entitled "System, Apparatus, and Method for Fastening Tissue," and patent application Ser. No. 11/345,208 filed Jan. 31, 2006 and entitled "System, Apparatus, and Method for Fastening Tissue," the entire contents of which are expressly incorporated herein by reference.

In light of the foregoing, there is presently a need for improved systems for remotely joining tissue pieces. More specifically, there is a present need for an improved method, apparatus, and system for remotely and securely joining tissue pieces with suture. The current invention meets this need.

BRIEF SUMMARY OF THE INVENTION

The present invention solves the problem of effectively joining tissue pieces using a suture and clip.

The present invention utilizes a clip having a generally tubular shape, with an inner lumen passing through the tube. The inner lumen is sized and configured so that one or more lines of suture may pass therethrough. The clip has an open configuration wherein the inner lumen is generally unobstructed, and a closed configuration wherein the inner lumen is at least partially obstructed so that suture line(s) passing therethrough are prevented from moving in one or more directions.

In one embodiment of a clip according to the invention, the clip may be configured to assume a bent configuration, wherein the clip is bent at one or more hinging points. The bent configuration creates a more convoluted pathway for the suture, and can include one or more crimping points that help to secure any suture lines therein.

A clip according to the invention may include one or more obstructions configured to extend into the inner lumen. The obstructions may be permanently positioned within the lumen, or may be movable so that they can extend into the lumen to a greater or lesser extent. In one embodiment, one or more tab-like obstructions are configured to extend into the inner lumen of the clip. As the clip assumes its bent configuration, the bending of the clip can force the tab-like obstructions into (or further into) the lumen, and/or to assume a more secure position where the tab-like obstructions are less likely to be pushed outward from the lumen. The tab-like obstructions may be configured to extend into the inner lumen when the clip is in its bent configuration. The tab-like obstructions may be configured to extend into the inner lumen of the clip when the clip is in its open (i.e., non-bent) configuration.

The clip may be formed from suitable biocompatible material, including, for example, Nickel-Titanium or other shape-memory alloys, stainless steel, titanium, other metals, various plastics, and other biologically-compatible materials. The clip can also be formed from bioresorbable materials, which can be used with bioresorbable suture to form a clip and suture combination that will dissolve or otherwise be absorbed into the body over time.

In a first embodiment, the clip is formed from shape-memory and/or pseudo-elastic materials such as nickel-titanium. The obstructions and hinge-like bends are movable so that the extent of their blocking the inner lumen varies to a lesser and greater extent. The clip may be formed such that it is biased toward its closed (i.e., bent) shape, including biasing of the tabs extend into and/or otherwise obstruct at least part of the clip inner lumen, when the clip material is in the austenite condition. With the clip shape-memory material in its austenite state, the bend (or bends) is at its greatest and the obstructions extend into the inner lumen to their greatest extent, so that the clip is in a "locked" configuration wherein the bend(s) and obstructions block movement of any suture line or lines passing through the inner lumen. The austenite state can be set to occur when the clip is generally unstressed and at human body temperature, so that the clip when deployed in the patient's body will be biased toward its locked configuration. The clip may also be formed such that the bends and/or tabs, when subject to sufficient stress such as a bending moment, are stressed into a martensite condition wherein the clip is physically held in an open configuration (i.e., with the clip inner lumen generally unobstructed), but once the stress is removed the bends and tabs will return to their austenite condition where they block the clip inner lumen.

The obstructions may be integrally formed with or from the generally tubular body. For example, the obstructions may be tabs cut from the tubular body and then bent or otherwise rotated into the inner lumen to block the inner lumen. The obstructing tabs may be formed from generally horseshoe-shaped cuts in the wall of the tubular body. The tabs can be sized, shaped, positioned, and/or otherwise configured to extend into the inner lumen to varying amounts, depending on the particular application. For example, a tubular structure with relatively thin suture lines passing therethrough may require larger tabs that can extend to a greater extent into the body lumen. Such tabs may be sized so that, when bent into the inner lumen, they extend across 50% or more of the diameter of the inner lumen.

The tubular body can include multiple tabs or similar obstructions. Where multiple tabs are present, they may be positioned at various locations along and around the tubular body. For example, they may be positioned at various distances along the length of the body, and/or may be positioned in various configurations around (e.g., on the same side or on opposing sides) the circumference of the tubular body. The tabs may also be configured to take advantage of the bending of the clip, so that one or more tabs interact with other clip structures (or with other tabs) when the clip is in the bent configuration. For example, two tabs may be configured to be independently movable when the clip is in the open (non-bent) configuration, but to engage against each other to "lock" each other in a desired position when the clip is in the closed (bent) configuration.

The clip can be formed in various ways. In one embodiment, an elongated tube is provided. The elongated tube is cut to a desired length to form the generally tubular body of the clip. The tabs are cut into the generally tubular body (if the tab cutting occurs after the elongated tube has been cut into individual tubular body lengths), or into the elongated tube (if the tab cutting is performed prior to the elongated tube being cut into individual generally tubular body lengths). The cutting of the tube and/or tabs to form the clip can be performed via laser cutting and/or other methods. After the tabs are cut, they are then bent or otherwise manipulated inward so that they obstruct the inner lumen, and the clip is bent at the desired hinge-points to create the desired closed (i.e., bent) clip configuration.

The clip may be deployed using various devices and/or procedures, such as a fastener catheter which may or may not have an integral suture-cutting apparatus. The fastener catheter may be configured to selectively apply stress to the clip, such as the application of force to move and/or hold a biased clip in a straightened (i.e., non-bent) configuration and to move and/or hold the clip engagement tabs out of the clip inner lumen and into general alignment with the clip outer wall.

In a method according to the invention, the user deploys suture through tissue within a patient's body, leaving one or more suture leads that pass out of the patient's body. A catheter and clip assembly according to the invention is advanced into the patient's body along the suture leads, the clip is positioned at a desired position on the suture adjacent the tissue, the catheter deploys and/or releases the clip at the desired position (whereby the clip assumes its closed configuration and locks the suture in place), and the catheter then cuts the suture leads at a position near the tissue. Alternatively, the suture cutting may be performed by a different catheter or other suture Cutting device.

Other objects, features, and advantages of the present invention will become apparent from a consideration of the following detailed description.

BRIEF DESCRIPTION OF THE DRAWINGS

FIG. 1 depicts a side view of a catheter and fastener assembly according to an embodiment of the invention;

FIGS. 2a and 2b show a perspective view of components of a catheter distal portion of an embodiment of the present invention;

FIG. 2c shows a perspective view of the catheter distal portion of the embodiment from FIGS. 2a and 2b assembled and having a fastener attached thereto;

FIGS. 3a, 3b, 3c, and 3d depict side, top, perspective, and distal end views, respectively, of a fastener in an open configuration according to an embodiment of the invention;

FIGS. 5a-5c depict side views of a catheter distal portion with a fastener and suture according to an embodiment of the invention;

FIGS. 7a-7f depict side (solid), side (cross section), top, bottom, perspective, and end views, respectively, of a fastener in an open configuration according to an embodiment of the invention;

FIGS. 8a-8e depict side (solid), side (cross section), top, bottom, and perspective views, respectively, of the fastener of FIGS. 7a-7f in a closed configuration;

FIG. 9 depicts a side view, in cross section, of a fastener according to an embodiment of the invention;

FIG. 10 depicts a plan view of a cut-out pattern for a fastener according to an embodiment of the invention;

FIGS. 13a and 13b depict cross-sectional side and end views, respectively, of a fastener in an open configuration according to an embodiment of the invention;

FIGS. 14a and 14b depict cross-sectional side and end views, respectively, of the fastener of FIGS. 13a and 13b in a bent (closed) configuration);

FIGS. 15a and 15b depict cross-sectional side and end views, respectively, of a fastener in an open configuration according to an embodiment of the invention;

FIGS. 16a and 16b depict cross-sectional side and end views, respectively, of the fastener of FIGS. 15a and 15b in a bent (closed) configuration).

DETAILED DESCRIPTION OF THE INVENTION

Figure 4:
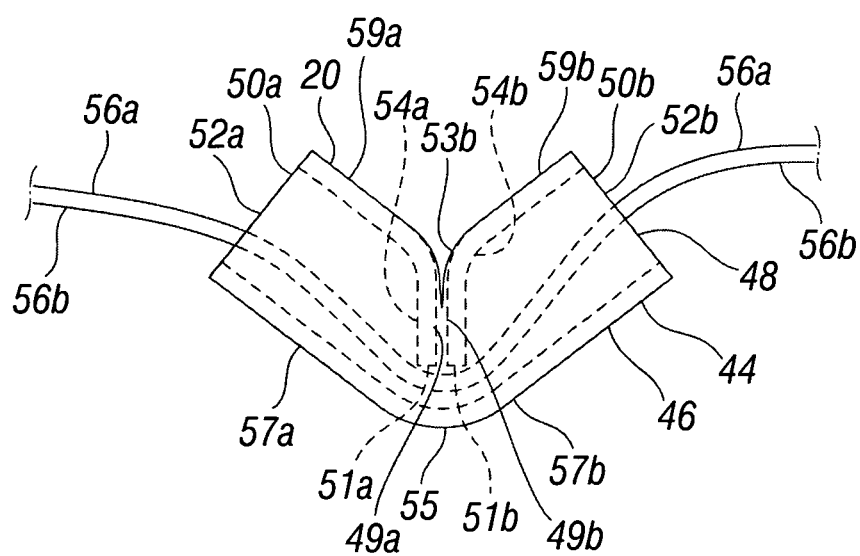
FIG. 4 depicts a side view of a fastener in a closed configuration with suture according to an embodiment of the invention.

The invention is an apparatus, system, and method for joining tissue via suture. More specifically, the invention provides for percutaneous or other minimally-invasive techniques of securing suture to tissue via a fastener clip.

FIG. 1 depicts an embodiment of a fastener catheter 10 according to an embodiment of the invention. The fastener catheter 10 has a generally tubular main catheter body 12, a proximal end 14, and a distal end 16. The proximal end 14 includes a handle knob 18. The distal end 16 includes a suture fastener clip 20 positioned thereon. The fastener catheter 10 may be manufactured in a variety of shapes, sizes, lengths, widths, and biologically-compatible materials as desired for a particular application.

The generally tubular catheter main body 12 has a longitudinal inner lumen 22 therethrough which terminates in a distal opening 24 having a surrounding edge 25. A longitudinally slidable inner body 26 is slidably positioned within the main body 12. The inner body 26 includes an inner tubular member distal end 28 which extends out of the main body distal opening 24. The inner tubular member distal end 28 itself includes an inner tubular member distal opening 30, which leads to an inner body lumen 32. These and other features are depicted in additional detail in FIGS. 2a-2c, which illustrate (in exploded fashion in FIGS. 2a-2b, and assembled in FIG. 2c), distal portions of the fastener catheter 10.

The inner body 26 includes a suture recess 34 formed in the side thereof, which in turn is in communication with the inner body lumen 32. Inner body 26 also includes a pin 36 extending radially outward therefrom. The main catheter body 12 has a cutting recess 38 formed in an axial side thereof and a cutting member 40 which, in the embodiment depicted, is on a proximal edge of cutting recess 38. A pin recess in the form of slot 42 extends parallel to the axis of the main body 12 and radially through to main body lumen 22. The slot 42 is thus configured to receive pin 36 in sliding relation.

In FIG. 2c, the inner body 26 is slidably positioned within main catheter body 12, such that suture recess 34 is in alignment with cutting recess 38. Pin 36 is in slidable communication with slot 42 thereby permitting relative linear motion, but preventing relative rotational motion, between inner body 26 and main body 12. A fastener clip 20 is positioned on the inner body distal end 28, which protrudes from the main body distal opening 24. The fastener clip, which is depicted in greater detail in FIGS. 3a-3d, includes a generally tubular body 44 having an outer wall 46, an inner lumen 48, a clip distal opening 52a, a clip proximal opening 52b, and engagement tab 54. As depicted in FIG. 2c, the fastener clip 20 has been placed on inner member distal end 28 in its open configuration wherein the clip body 44 is generally straight (i.e., unbent) and the engagement tab 54 is deflected radially outward until it is generally flush with the clip outer wall 46. Accordingly, the fastener clip 20 is secured to the inner body distal end 28 by means of the frictional engagement of the engagement tab 54 and clip body 44 against the outer surface of inner body 26. Suture 56 extends from the fastener clip 20, with suture leads 56a and 56b extending through the clip inner lumen 48 via the clip distal opening 52a, engagement tab 54, and proximal opening 52b, passing through catheter inner member distal opening 30 and inner member lumen 32, exiting the inner member 26 via suture recess 34, and exiting the side of main body 12 through cutting recess 38.

Note that a clip according to this particular invention may have a (relatively gentle) curve along its length but still be considered "generally straight." The term "generally straight" is used to refer to a configuration wherein the clip does not have a relatively tight bend sufficient to cause crimping of the inner lumen.

FIGS. 3a through 3d illustrate a fastener clip 20 of the present invention in an "open" configuration, while FIG. 4 depicts the fastener clip 20 in a "closed" or "locked" configuration. The fastener clip 20 may be manufactured from a variety of materials including, for example, nickel-titanium alloys, shape-memory alloys, stainless steel, titanium, various plastics, and other biologically-compatible materials. Fastener clip 20 has a generally tubular body 44 and an outer wall 46, and includes a distal end 50a having a distal opening 52a leading to an internal attachment lumen 48 extending axially through the fastener clip 20 to a proximal opening 52b at the proximal end 50b. The fastener clip 20 includes one or more engagement tab(s) 54a, 54b formed in the fastener clip 20 and configured to leave the inner lumen relatively unobstructed when in the "open" configuration as depicted in FIGS. 3a-3d, and to at least partially obstruct the inner lumen 48 when in a "closed" configuration, as depicted in FIG. 4. The fastener clip 20 includes notches 53a, 53b cut adjacent the tabs 54a, 54b, with the notches 53a, 53b helping to create a hinge-point 55 about which the proximal half 57a and distal half 57b of the clip body 44 can bend. Each tab 54a, 54b has a tab outer surface 49a, 49b, a tab free end 51a, 51b, and is anchored to the rest of the clip outer wall 46 via a tab base 59a, 59b. In the particular embodiment depicted in FIGS. 3a-3d, the tabs 54a, 54b each have a length extending from the tab base 59a, 59b to the respective tab end 51a, 51b. The tabs 54a, 54b extend lengthwise (from tab base 59a, 59b to respective tab ends 51a, 51b), e.g., longitudinally, along the length of the clip 20. Distal tab 54a includes a tab base 59a which is on an opposite end of the tab 54a (and also positioned toward the distal end (with respect to the clip distal end 50a and clip proximal end 50b) from the tab free end 51a is proximal (and at an opposite end) of the tab 54a from the tab base 59a . Tab 54b is a mirror image of tab 54a (as most clearly seen in FIG. 3b), with tab base 59b at a proximal end of the tab 54b, and the tab free end 51b is at the opposite (and distal) end of the tab 54b from the tab base 59b. Note that both tabs 54a, 54b are depicted as being cut from the same side of the clip 20, wherein a side is defined as extending from a distal end 50a to a proximal end 50b of the fastener clip 20. As per accepted use among those skilled in the art when describing generally tubular and/or cylindrical structures, the term "end" of the clip is used herein to refer to distal and/or proximal ends of the clip, and the term "side" of the clip is used herein to refer to a portion of the clip wall extending from the clip proximal end to the clip distal end. The term "opposing sides" is used to distinguish a first side of the clip as compared to another side which is generally positioned about 180 degrees around the circumference of the generally tubular clip body from the first side. (For example, in the embodiment depicted in FIGS. 7a-7b, the tabs 54a, 54b are both cut from the "same side" of the clip 20, but the stress-relief lines 68 are cut from an "opposing side" of the generally tubular body of the clip 20 from the tabs 54a, 54b.) In the open configuration depicted in FIGS. 3a-3d, the free ends 51a, 51b are adjacent to each other, and the tab bases 59a, 59b are some distance apart, and more specifically the tab bases 59a, 59b are positioned closer to the clip distal end 50a (for tab base 59a of distal tab 54a) and closer to the clip proximal end 50b (for tab base 59b of proximal tab 54a) than are the respective free ends 51a, 51b of the tabs 54a, 54b. In this open configuration depicted, the free ends 51a, 51b are adjacent but separated by a break in the outer wall, which in the embodiment of FIGS. 3a-3d is a gap 61.

The clip body 44, distal opening 52a, proximal opening 52b, inner lumen 48, and engagement tabs 54a, 54b are sized and configured (when the clip body 44 and engagement tabs 54a, 54b in the "open" configuration of FIGS. 3a-3d)to slidingly receive one or more suture leads therein. Prior to deployment, the clip body 44 is moved to its open (i.e., straightened) configuration, and the engagement tabs54a, 54b are moved to their "open" configuration by being deflected radially out of the inner lumen 48 such that the engagement tabs 54a, 54b are essentially flush with the fastener outer wall 46, thereby leaving the inner lumen 48 essentially unobstructed, or at least unobstructed to the extent necessary for the suture lines to slidingly pass within the lumen 48. As was depicted in FIG. 3a, the inner lumen 48 (with the clip body 44 straightened and the engagement tabs 54a, 54b in their open configuration) provides a relative large and relatively unobstructed passage sufficient to permit suture leads to slide therethrough.

Upon deployment, i.e. after the suture leads 56a, 56b have been retracted and/or tightened to their desired position and the fastener clip 20 advanced to it's desired deployment position, the clip body 44 is bent such that the overall shape of the clip is generally that of a "V" (which may include stressing a plastically deformable clip to assume the bent configuration, or permitting a biased clip to spring back to the bent configuration), with clip bending occurring along a hinge point 55, and the engagement tabs 54a, 54b are deflected or permitted to spring back into the inner lumen 48 toward the hinge point 55 such that the inner lumen 48 is at least partially blocked, as depicted in FIG. 4. Note that when the fastener clip 20 is brought into the closed configuration depicted in FIG. 4, the tab bases 59a, 59b as well as the opposing ends 50a, 50b of the clip are brought toward each other by the bending movement of the generally tubular body 44 about the hinge-point 55. The tab free ends 51a, 51b are moved into the internal attachment lumen 48 toward the suture leads 56a, 56b. Suture leads 56a, 56b are held fast within the closed clip 20, with the engagement tabs 54a, 54b engaging against and securing the suture leads 56a, 56b against the clip body 44. The "closed" engagement tabs 54a, 54b and bent clip body 44 cause the suture leads 56a, 56b passing therethrough to adopt a "serpentine" path through the clip inner lumen 48. This serpentine path, combined with the friction on the suture from the clip body 44 and engagement tabs 54a, 54b, serves to lock the suture 56a, 56b in place and prevent longitudinal movement thereof within the clip lumen 48. The suture 56a, 56b is thus held by the combination of tab 54a, 54b to clip inner wall interaction/forces and by the tortuous path that the bent clip body 44 and tabs 54a, 54b force the suture leads 56a, 56b to follow, which provides more surface area contact with the suture 56a, 56b to increase retention. Note also that the bending of the clip body 44 holds the outer surfaces 49a, 49b of the tabs 54a, 54b against each other, so that neither of the tabs 54a, 54b can bend back outwardly without engaging against the other tab.

In the embodiment of FIG. 4, the suture lines 56a, 56b are depicted as being relatively thin as compared to the clip lumen 48. However, depending on the particular application, suture that is of a much greater thickness would be used with a clip according to the invention. If used with thicker suture (s), a clip 20, and particularly the tabs 54a, 54b, might assume a somewhat different shape once deployed. With a thicker suture line or lines, the tabs 54a, 54b would each be forced back outward (i.e., toward their "open" configuration") by the suture, but the bending of the clip body 44 and the resulting interaction between the tabs 54a, 54b will prevent excessive tab movement, and the suture will still be held securely within the clip body 44.

Depending on the particular embodiment, including the materials from which a particular fastener is made, the clip body (and the bend therein) as well as the engagement tab(s) may be biased to spring toward a desired position, which may be either the closed configuration or the open configuration, depending on the particular application.

FIGS. 5a-5c depict, in various configurations, deployment of a clip 20 from the distal end 16 of a catheter 10 according to an embodiment of the invention. FIG. 5a depicts the catheter inner body distal end 28 extending from catheter main body distal opening 24, with a fastener clip 20 positioned on the inner body distal end 28. A suture line 56 extends through tissue portions 58a, 58b into the assembly with suture leads 56a, 56b exiting the inner member 26 via suture recess 34, and exiting the side of main body 12 through cutting recess 38. In the particular embodiment depicted, the clip 20 is biased towards its closed configuration, and the inner body distal end 28 of the catheter 10 physically holds the clip 20 in its open configuration.

In FIG. 5b, the catheter inner body distal end 28 has been retracted into the main body distal opening 24. With the inner body distal end 28 retracted, the fastener clip 20 has been released from the catheter 10. As the inner body distal end 28 was retracted, the fastener clip 20 engaged against the distal edge 25 of the main body distal opening, 24 and was forced off of the inner body distal end 28 at a position adjacent the tissue portions 58a, 58b. With the fastener clip 20 freed from the catheter, the clip 20 assumes its closed (i.e., bent) configuration, with the clip body 44 bent and the engagement tabs 54a, 54b projecting inward to at least partially obstruct or even to completely close the clip inner lumen 48 while engaging the suture leads 56a, 56b. With the fastener clip 20 in this closed configuration, the suture leads 56a, 56b are held fast and cannot move longitudinally within the fastener clip 20. The suture leads 56a, 56b are thus held by the combination of tab to inner wall interaction/forces and by the tortuous path that the tabs 54a, 54b and bent clip body 44 force the suture leads 56a, 56b to follow, which provides more surface area contact with the suture leads 56a, 56b to increase retention. Note that the suture leads 56a, 56b still pass into the catheter 10, exiting the inner body 26 via suture recess 34 and exiting the side of main body 12 through cutting recess 38.

FIG. 5c depicts the catheter inner body 26 retracted even further within the catheter main body 12. As the inner body 26 was retracted, the suture leads 56a, 56b were caught in the engagement between the cutting member 40 of the main body 12 and a suture recess distal edge 35 of the inner body 26. The engagement of the cutting member 40 with the suture recess distal edge 35 cuts the suture leads 56a, 56b, allowing the user to remove the excess portions 60a, 60b thereof Although the embodiment depicted in FIGS. 5a-5c includes a cutting member 40 on the main body, a cutting member could be placed elsewhere, either in addition to or in lieu of the main body cutting member. For example, a cutting member could be placed on the suture recess distal edge 35 of the inner body 26. Or both the suture recess distal edge 35 and the main body cutting member may be unsharpened edges, with the suture being cut by the sheering force created by the cooperation between the relatively unsharp edges.

Figure 6:
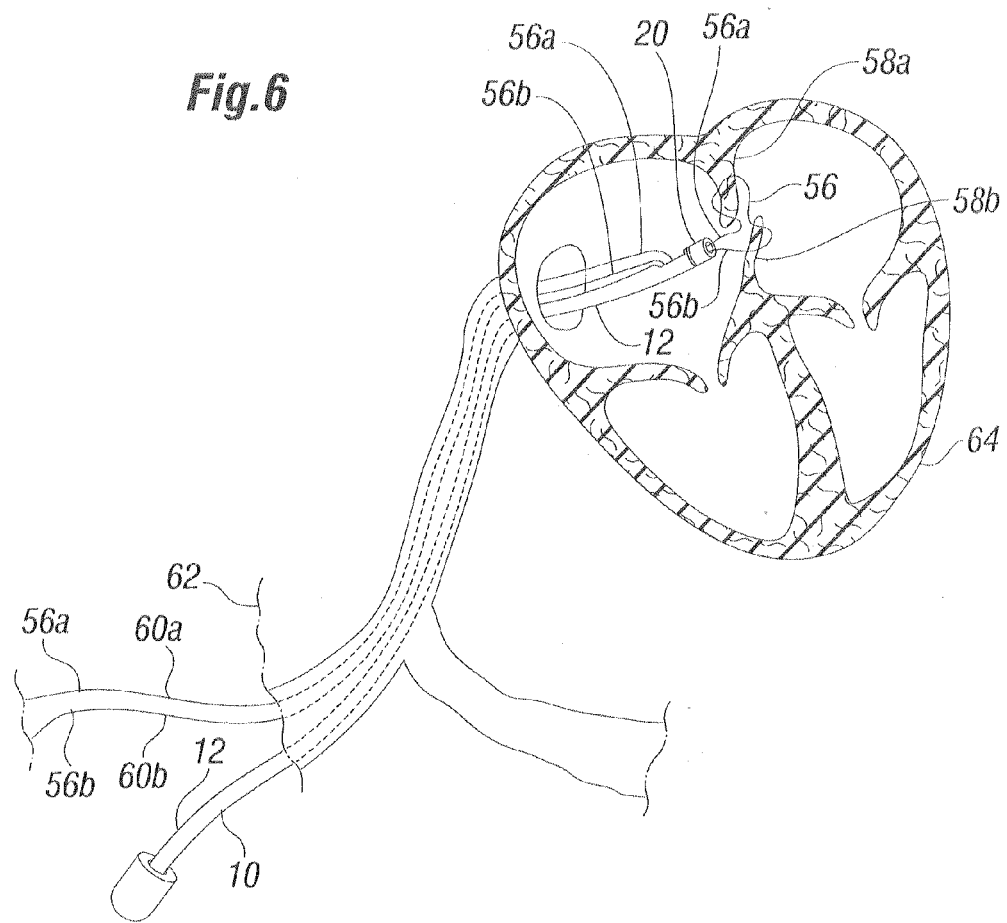
FIG. 6 illustrates a catheter advanced within a patient's vasculature and adjacent tissue pieces to be joined according to an embodiment of the invention.

FIG. 6 depicts the fastener catheter 10 deploying a fastener clip 20 at a desired location in a patient's body 62. In the embodiment depicted, the suture 56 has previously been passed through the desired tissue structures 58a, 58b within the patient's body 62, which in the embodiment depicted is tissue with the patient's heart 64, and specifically tissue adjacent an atrial septal defect, such as a patent foramen ovale (PFO). With the suture 56 passing through the tissue 58a, 58b and the suture leads 56a, 56b passing out of the patient's body 62, the user can advance the fastener catheter 10 into the vicinity of the tissue 58a, 58b, as shown in FIG. 6. The fastener catheter will advance along the suture leads 56a, 56b and, if present, along a guidewire (not shown). Note that in the particular embodiment depicted, the suture 56 has been passed twice through each portion of tissue 58a, 58b, which will tend to hold the adjacent wall-like tissue structures 58a, 58b in side-to-side relation, with the clip 20 positioned therebetween, once the suture 56 is tightened and secured with the clip 20.

Various methods and/or systems can be used to pass the suture through the desired tissue. Moreover, although FIG. 6 depicts the invention used to repair a PFO, the invention can also be used in other procedures, including tissue treatments such as so-called "edge-to-edge" mitral valve repairs involving edge-to-edge suturing of adjacent mitral valve leaflets. In another procedure, embodiments of the system may be used to occlude a left atrial appendage for decreasing the risk of arterial embolism. In one preferred procedure, tissue along the ostium of the left atrial appendage is sutured together to prevent blood from flowing in and out. This procedure is preferably performed using a transseptal approach and may be performed after delivering an expandable device into the left atrial appendage for filling the volume and further preventing the formation of thrombus. In another method of use, the system may be used for occluding fallopian tubes in a minimally-invasive sterilization technique. In this procedure, the system is advanced into a fallopian tube and suture is applied to pull opposing walls together, thereby blocking the tube. In still other applications, the system may be used to treat organ prolapse, such as uterine or bladder prolapse. This procedure may be used to pull tissue together in a percutaneous procedure to treat prolapse by providing additional support at locations wherein muscles and/or ligaments have become stretched or have been otherwise damaged.

Additional information on procedures for which the current invention can be applicable are disclosed in the following references, the entire contents of which are expressly incorporated herein by reference: U.S. Pat. No. 6,626,930 issued to Allen et al.; U.S. patent application Ser. No. 10/106,583, filed Mar. 26, 2002 and entitled, "Sequential Heart Valve Leaflet Repair Device and Method of Use"; U.S. patent application Ser. No. 10/233,879, filed Sep. 3, 2002 and entitled "Single Catheter Mitral Valve Repair Device and Method"; U.S. patent application Ser. No. 10/389,721, filed Mar. 14, 2003 and entitled "Mitral Valve Repair System and Method of Use"; and patent application Ser. No. 11/174,143, filed Jun. 30, 2005 and entitled "System, Apparatus, and Method for Repairing Septal Defects."

Referring again to FIG. 6, the user can initially tighten the suture 56 to determining whether the suture 56 is properly positioned in accordance with the desires of the user in the particular application. The advancement of the fastener catheter 10, combined with the user holding (and possibly pulling on) the suture leads 56a, 56b, causes the suture 56 to tighten. The user can verify the effectiveness of the tightened suture 56 by monitoring various patient functions. For example, the user may confirm the result by monitoring blood flow using radiopaque dyes combined with fluoroscopy. If the user is dissatisfied with the results when the suture 56 is initially tightened, the user can remove the suture 56 entirely From the patient's body 62 and repeat the suture deployment to try to achieve a better positioning of suture. If, however, the user is satisfied with the results, the user can release the fastener clip 20 from the catheter 10. Once the fastener clip 20 is released, the fastener clip 20 securely holds the suture leads 56a, 56b. The user can then cut the suture leads 56a, 56b and remove the excess suture 60a, 60b by simply pulling the excess suture 60a, 60b out of the patient's body 62. The user then withdraws the fastener catheter 10 from the patient, leaving the suture 56 and suture fastener clip 20 in place in the desired tissue. The guidewire, if present, is also removed.

Note that the number, shape, and configuration of the engagement tabs and hinge points on a particular clip can vary, depending on the particular application. For example, the engagement tabs can be positioned on opposing sides of the clip, on the same side of the clip, in a spiral pattern about the clip body, etc. Similarly, the hinge points can be positioned on opposing sides of the clip, on the same side of the clip, in a spiral pattern, etc.

FIGS. 7a-7f and 8a-8e depict, in open and closed configurations, respectively, a further embodiment of the invention. The fastener clip 20 is initially formed from a generally tubular body 44, such as a portion of nitinol hypotube into which the desired pattern of tabs 54a, 54b, tab stress cutout windows 66, bending notches 53, and stress-relief cuts 68, etc., is formed. The tabs have free edges 51a, 51b which are adjacent; however, a break, such as the gap 61, in the wall of the generally tubular body 44 is positioned between the adjacent free edges 51a, 51b. The fastener clip includes distal and proximal ends 50a, 50b having distal and proximal openings 52a, 52b.

Note that the clip 20 including the pattern of tabs 54a, 54b, etc., can be formed in various ways, depending on the particular application. For example, injection molding, die and coining, laser cutting, machining, and shape setting can be used, alone or in combination, depending on the particular clip configuration and materials. In one embodiment, the pattern is formed by laser cutting the desired pattern into a portion of a hypotube or other generally tubular body. FIGS. 7a-7f depict the generally tubular body 44 after the desired pattern has been cut into the generally tubular body, but before the tubular body has been bent and before the tabs 54a, 54b have been bent or otherwise moved and set into position to block the inner lumen 48. The configuration depicted in FIGS. 7a-7f also corresponds with the "open" configuration of the clip 20.

FIGS. 8a-8e depict the clip 20 of FIGS. 7a-7f, but with the clip body 44 bent and the tabs 54a, 54b have been bent into and set in their "closed" position, wherein the inner lumen 48 is at least partially blocked. The notches 53 on either side of the clip 20 create a hinge point 55 about which the clip 20 can easily bend. (Note that, although the term "hinge point" is used herein, the actual bending may occur over a relatively large area, as is shown in the embodiment of FIGS. 8a-8e.) The tab stress cutout windows 66 enhance the flexibility while maintaining strength of the tabs 54a, 54b, and also reduce stress on the hinge-like portion, such as the tab bases 51a, 51b of the embodiment depicted, where each tab 54a, 54b connects to the generally tubular body 44 of the clip 20. The stress relief lines 68, which are on the same side of the clip 20 as the hinge point 55, help to relieve stress that might build up on that side of the clip body 44 as the clip 20 assumes its bent configuration. In the embodiment of FIGS. 8a-8e, the free portions of the engagement tabs 54a, 54b are directed toward each other, and are both on an opposite side of the clip body 44 from the hinge point 55. As seen in FIG. 8b, the opposing ends 50a, 50b of the clip are brought toward each other, the free edges 51a, 51b of the tabs are driven into the inner lumen 48 toward the opposite side of the clip 20, and the engagement tabs 54a, 54b engage against each other when the clip is in the bent configuration in this particular embodiment.

FIG. 9 depicts, in cross section, a side view of a clip 20 according to an embodiment of the invention. Tile clip 20 includes a single tab 54 positioned across from a hinge point 55. The clip 20 includes a beveled inner edge 70 at one or more of the clip openings, such as the clip distal opening 52a as depicted. The beveled inner edge 70, which in the embodiment depicted is at an angle of about 45 degrees, can assist in threading suture into the clip 20 through the clip distal opening 52a. The clip 20 can also include one or more generally semi-circular openings 72 at one or more openings, such as the clip proximal opening 52b. The semi-circular openings 72 can aid in processing of the clip during manufacture, e.g., permitting easy alignment and holding of the clip 20 during bending and/or shape setting of the clip body 44 and tabs 54a, 54b, etc. After clip manufacturing is complete, the semi-circular openings 72 call interact with corresponding structure on the catheter distal end to assist in alignment and positioning of the clip 20 on the catheter distal end.

The clip 20 depicted in FIG. 9 also includes a window-like opening 74 aligned opposite to the free edge of the tab 54, positioned so that when the tab 54 extends into the inner lumen 48 the free edge of tile tab 54 can rest within the window-like opening 74, but without extending out of the clip 20 itself. The window-like opening 74 permits tab 54 to be bent or otherwise positioned so that the tab free edge extends across and just beyond the inner lumen 48, thereby compensating for any backward tab movement (either through material recovery or outward pressure from the suture lines, etc.) that might occur after the tab 20 is initially deployed to its closed configuration. Note that a window-like opening such as element 74 from FIG. 9 could be positioned at or near a hinge point, so that the window-like opening serves multiple purposes: receiving the tab free edge, relieving stress that might develop adjacent the hinge point, and providing for relatively easy bending or flexing of the clip body about the hinge point.

FIG. 10 depicts a cutout pattern (in flattened or unrolled configuration) for creating a clip according to an embodiment of the invention. The generally elliptically-shaped portion 76 of each the tabs 54a, 54b (with 54b having a dashed portion depicting an imaginary completion of the "ellipse" that forms the actual tab) has a width W (i.e., minor axis) that is approximately equal to (but still slightly less than) the diameter of the clip inner lumen 48. The generally elliptical shaped portion 76 has a length L (i.e., major axis) that is greater than the diameter of the clip inner lumen 48. These dimensions permit each tab 54a, 54b, when in the closed configuration, to fit within the clip inner lumen 48 and still close off essentially the entire diameter of the clip inner lumen 48, thereby securely holding any suture passing therethrough.

Note that because the pattern of tabs and windows may have been cut in a radial manner into the generally tubular body 44 of the clip 20, the tabs 54a, 54b each have an inner surface having an "inner" elliptically-shaped portion that is somewhat smaller in width than its corresponding "outer" elliptically-shaped portion 76 discussed above. Accordingly, the relatively narrow width of each tab's respective inner elliptically-shaped portion may only partially obstruct the inner lumen 48. However, the tab outer surface has the full width W of the elliptically-shaped portion 76 shown in FIG. 10, and it is this width (W) of the "outer" elliptically-shaped portion 76 that obstructs the remaining diameter of the inner lumen 48 when a tab 54a, 54b extends into the inner lumen 48.

The dimensions of the clip can vary depending on the particular application. In one embodiment, a clip 20 such as that depicted in FIGS. 7a-7f has a length of about 0.13 inches, an inner lumen diameter of about 0.030 inches, and an outer diameter of about 0.046 inches. A clip of this size can receive and secure multiple suture lines having various diameters, including sutures having diameters ranging from 0.006 to 0.008 inches. Other clip dimensions are also within the scope of the invention, with the clip dimensions varying depending on aspects of the particular application, e.g., suture type and diameter, the type of tissue to be repaired, the number of suture lines being secured by the clip, etc. Additionally, although the particular embodiment depicted have used the clip to secure two suture lines, a clip according to the invention could be used to secure a single suture line or multiple suture lines. For multiple suture lines, two or more of the multiple suture lines could be portions of a common suture line. For example, a clip could be used to secure four suture lines, with two of those suture lines being opposing portions of a first common suture line and the other two suture lines being opposing portions of a second common suture line, Note that the embodiments depicted are only a few examples of many that are within the scope of the invention. Depending on the particular embodiment, the tab and other cut-outs could be formed in various shapes, and they could be aligned in a common direction with other cutouts, be in opposite directions of alignment, and/or could be positioned in various directions along the clip outer wall.

Figure 11A:
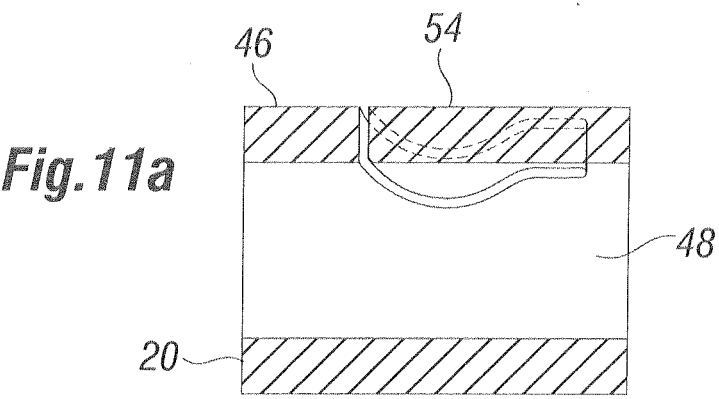
FIG. 11a-11c depict side views, in cross-section, of fasteners according to various embodiments of the invention.
Figure 11B:
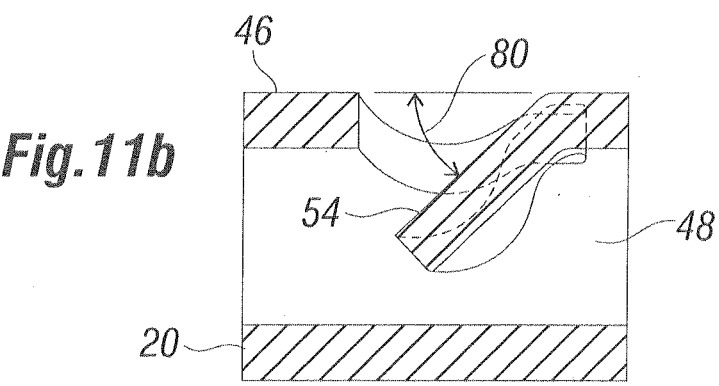
Figure 11C:
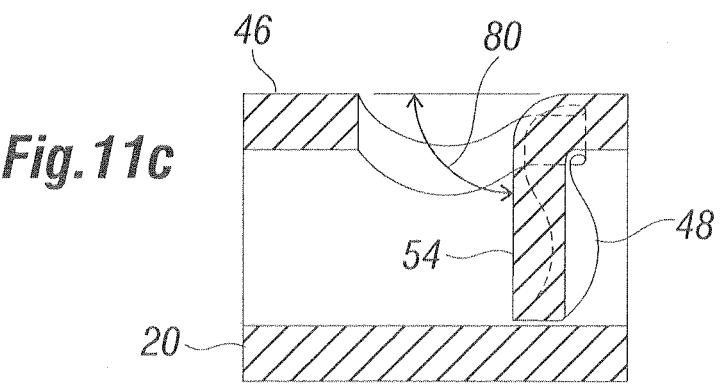

FIGS. 11a-11c depict in cross-section an engagement tab 54 in various configurations. In the embodiment of FIG. 11a, the engagement tab 54 is generally aligned with the clip outer wall 46, so that the clip inner lumen 48 is generally unobstructed. In FIG. 11b the engagement tab 54 is positioned to extend partially into the lumen 48, with the angle 80 between the engagement tab 54 and adjacent portion of the clip outer wall 46 being on the order of 45 degrees. FIG. 11c depicts the engagement tab 54 extending to a maximum extent into the clip lumen 48, with the angle 80 between the engagement tab 54 and adjacent portion of the clip outer wall 46 being on the order of 90 degrees. Note that various angles 80 are within the scope of the invention, depending on the particular embodiment and such factors as the size of the suture, the size of the clip, the percentage of the inner lumen that is desired to be obstructed, the length of the engagement tab with respect to the inner diameter of the lumen, the bend added to the clip body 44, etc.

Figure 12A:
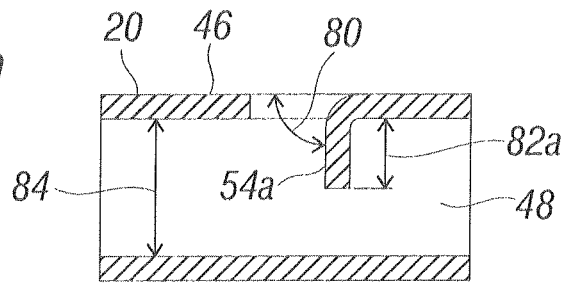
FIGS. 12a-12c depict side views, in cross-section, of fasteners according to various embodiments of the invention.
Figure 12B:
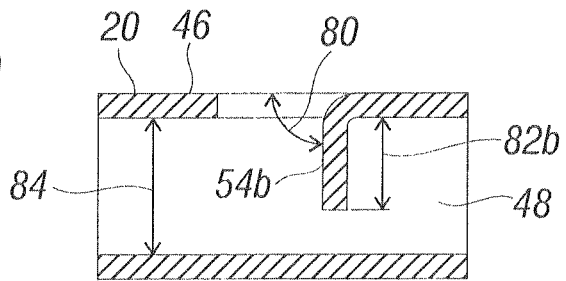
Figure 12C:
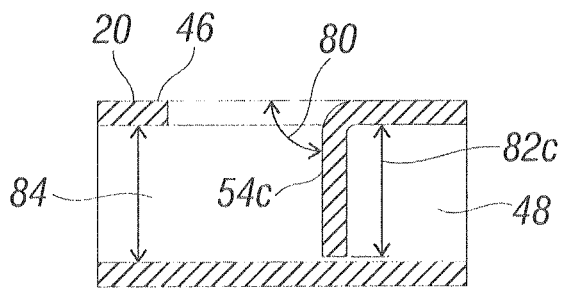

FIGS. 12a-12c depict clips 20 having various lengths 82 of engagement tabs 54. Although the embodiments of FIGS. 12a-12c are all depicted as having an angle 80 of about 90 degrees, it is noted that other angles are within the scope of the invention, as discussed above with respect to FIGS. 11a-11c. In FIG. 12a, the engagement tab 54a has a length 82a equal to about 50% of the clip inner lumen diameter 84. In FIG. 12b, the engagement tab 54b has a length 82b of about 75% of the clip inner lumen diameter 84, while in FIG. 12c the engagement tab 54c has a length 82c of about 100% of the clip inner lumen diameter 84. Note that, as with the angle 80, the engagement tab length 82 for a particular clip can vary depending on the particular application and still fall within the scope of the invention.

Note that the bending of the clip body 44 itself can effectively block a clip inner lumen, with or without engagement tabs such as those (54, 54b, 54c) depicted in FIGS. 12a-12c, etc. FIGS. 13a-13b and 14a-14b depict a clip 20 having a hinge point 55, but without tabs or other projections inside the inner lumen 48. In FIGS. 13a-13b, the clip body 44 is in its straight or open configuration, without any bending about the hinge point 55. The inner lumen 48 is seen in FIG. 13b as being essentially open and unobstructed adjacent the hinge point 55. In FIGS. 14a-14b, the clip 20 is in its bent or closed configuration, with a relatively sharp bend in the clip body 44 adjacent the hinge point 55. The inner lumen 48 is seen in FIG. 14b as being almost entirely blocked adjacent the hinge point 55. Note that although a single hinge point 55 and associated bend is depicted in FIGS. 14a-14b, a fastener clip according to the invention could include multiple hinge points and associated bends along the length of the fastener clip.

FIGS. 15a-15b and 16a-16b depict a clip having a hinge point 55 with inward-facing obstructions in the form of inner bumps 84 that extend into the clip inner lumen 48 at or adjacent the hinge point 55, In FIGS. 15a-15b, the clip 20 is in the open configuration, with the inner lumen 48 being generally unobstructed adjacent the hinge point 55 except for minimal areas covered by the inner bumps 84, as depicted in FIG. 15b, so that the inner lumen 48 has a size sufficient for suture to slidingly pass therethrough. FIGS. 16a-16b depict the same clip 20 in its closed configuration, wherein the clip body 44 is bent and has an almost flattened shape adjacent the hinge point 55, as depicted in FIG. 16b. With the bumps 86 engaging against each other and/or the clip wall, the inner lumen 48 is generally obstructed adjacent the hinge point 55 so that suture lying within the inner lumen 48 will be held fast.

Clips according to the invention may be formed from various biocompatible materials, including shape memory and/or pseudoelastic materials such as nitinol. In one embodiment a fastener clip is formed from nitinol (such as an alloy of nickel at 54.5-57% by weight with titanium accounting for the balance except for residual amounts (less than 0.05% each) of oxygen, carbon, and hydrogen) or another shape memory and/or pseudoelastic material, with the fastener clip formed so that the clip assumes its closed position (i.e., with the clip body in the bent configuration and the clip engagement tabs extending into the clip inner lumen) when in the austenite condition (i.e., when generally unstressed at body temperature). The nitinol can have an austenite finish temperature selected to match the particular application. In a medical suture clip, an austenite finish temperature of −5 degrees to +15 degrees Celsius may be selected.

A fastener clip may be formed from material that will assume its martensite condition when subjected to sufficient stress, such as the stress applied to the clip engagement tabs 54 and clip body 44 when the fastener clip 20 is mounted onto the catheter inner body distal end 28, as was depicted in FIG. 5a. In such an embodiment, the catheter inner body distal end 28 applies stress to the clip body 44 and clip engagement tabs 54, forcing the clip body 44 to be straight and the clip engagement tabs 54 into general alignment with the clip outer wall 46. The stressed material, including the bent material where the clip engagement tabs 54 meet the rest of the clip outer wall 46, is forced into its martensite condition. Then the stress is removed, such as where the fastener clip 20 is removed from the catheter 10 and catheter inner body distal end 28 as depicted in FIGS. 5b and 5c, the material returns to its austenite condition so that the clip body 44 assumes its bent shape and the clip engagement tabs 54 are biased inwardly to at least partially block the clip inner lumen 48.

While the invention has been described with reference to particular embodiments, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention not be limited to the particular embodiments disclosed herein, but that the invention will include all embodiments falling within the scope of the appended claims.

What is claimed is:

1. A clip for securing suture, the clip comprising:
a generally tubular body having a distal end, a proximal end, a length, an outer wall defining sides extending generally from the distal end to the proximal end, an inner lumen, a distal generally tubular portion, and a proximal generally tubular portion, and further comprising a first tab cut at least partially from the outer wall of the distal generally tubular portion of the generally tubular body, wherein the first tab comprises a first tab base at which the first tab is secured to the outer wall, the first tab further comprising a first tab free end, wherein the first tab base and the first tab free end are on opposing ends of the first tab and are longitudinally spaced away from each other along the length of the generally tubular body;
wherein the clip has a first configuration wherein the generally tubular body is relatively straight along its length, and the clip has a second configuration where a bend is formed at a hinge point along the length of the generally tubular body, wherein the distal generally tubular portion extends distally of the hinge point and the proximal generally tubular portion extends proximally of the hinge point, wherein the first tab base is longitudinally spaced away from the hinge point along the length of the generally tubular body, wherein the first tab free end is placed longitudinally adjacent the hinge point with respect to the length of the generally tubular body, wherein the generally tubular body, including the inner lumen thereof, assumes a general V-shape when the clip is in the second configuration, and wherein when the clip is in the second configuration the clip is no longer straight and the entirety of the distal generally tubular portion is bent out of longitudinal alignment from the proximal generally tubular portion about the hinge point, the bend creating a crimped region within the inner lumen at the hinge point so as to at least partially obstruct the inner lumen, wherein when the clip is in the second configuration the first tab extends at least partially into the inner lumen and into the inner lumen at the hinge point and within the crimped region.

2. The clip of claim 1, wherein the generally tubular body is formed from a memory material and is biased toward the second configuration.

3. The clip of claim 1, further comprising a second tab cut at least partially from the outer wall of the generally tubular body, wherein the second tab comprises a second tab base at which the second tab is secured to the outer wall, the second tab further comprising a second tab free end, wherein the second tab base and the second tab free end are on opposing ends of the second tab and are longitudinally spaced away from each other along the length of the generally tubular body, wherein the second tab base is longitudinally spaced away from the hinge point along the length of the generally tubular body, wherein the second tab free end is placed longitudinally adjacent the hinge point with respect to the length of the generally tubular body, wherein when the clip is in the second configuration the second tab extends at least partially into the inner lumen at the hinge point and within the crimped region.

4. The clip of claim 3, wherein the first tab and second tab are cut from the same side of the generally tubular body, the first tab has a first tab free end, the second tab has a second tab free end, and when the clip is in the first configuration the first tab free end is adjacent the second tab free end with no structure therebetween except a gap in the outer wall of the generally tubular body, and when the clip is in the second configuration the first tab and second tab both extend into the inner lumen with the first tab engaging into contact against the second tab.

5. The clip of claim 1, further comprising one or more notches in the outer wall, the notches configured to encourage bending of the generally tubular body at a position at or adjacent the hinge point.

6. The clip of claim 1, further comprising one or more stress relief cutouts on the outer wall.

7. A system for suturing tissue, comprising:
a clip comprising a generally tubular body having a length, a proximal generally tubular portion, a distal generally tubular portion, an outer wall, and an inner lumen, the clip further comprising a first tab formed from a generally horseshoe-shaped cut from the outer wall of the generally tubular body, the first tab comprising a first tab outer surface, wherein the first tab comprises a first tab base at which the first tab is secured to the outer wall, the first tab further comprising a first tab free end, wherein the first tab free end is on an opposing end of the first tab with respect to the first tab base, wherein the clip has a first configuration wherein the generally tubular body is generally straight along its length, and a second configuration wherein the generally tubular body forms a general "V"-shape and the inner lumen also forms a generally "V"-shape, wherein the bend is adjacent the first tab free end along the length of the generally tubular body but the bend is also displaced along the length of the generally tubular body from the first tab base, the bend creating a crimped region in the inner lumen so as to at least partially block the inner lumen, wherein when the clip is in the second configuration the first tab free end extends at least partially into the inner lumen and into the crimped region within the inner lumen, and wherein when the clip is in the second configuration the proximal generally tubular portion is rotated about the crimped region with respect to the distal generally tubular portion; and
a suture line passed through at least one portion of tissue, the suture line comprising first and second suture portions joined by an intermediate suture portion, wherein the first and second suture portions pass through the inner lumen of the clip.

8. The system of claim 7, wherein the clip is formed from a memory material and is biased toward the second configuration.

9. The system of claim 8, further comprising:
a clip delivery catheter, wherein the clip delivery catheter comprises a distal end configured to be advanced into a patient's body, to physically hold the clip in the first configuration, and to release the clip, wherein the clip delivery catheter further comprises a cutting element at the distal end configured to cut excess suture.

10. The system of claim 7, wherein the clip comprises a second tab formed from a generally horseshoe-shaped cut from the outer wall of the generally tubular body, the second tab comprising a second tab outer surface, wherein the second tab comprises a second tab base at which the second tab is secured to the outer wall, wherein the second tab base is displaced along the length of the generally tubular body from the bend, the second tab further comprising a second tab free end, wherein the second tab free end is on an opposing end of the second tab with respect to the second tab base, wherein when the clip is in the second configuration the second tab free end extends at least partially into the inner lumen and into the crimped region within the inner lumen, wherein the outer surface of the first tab and the outer surface of the second tab engage against each other when the clip is in the second configuration.

11. The system of claim 10, wherein the first tab is cut from the proximal generally tubular portion, the second tab is cut from the distal generally tubular portion, and the first tab and second tab are cut from the same side of the generally tubular body, and when the clip is in the second configuration the first tab free end is adjacent the second tab free end with no structure therebetween except a break in the outer wall of the generally tubular body.

12. A clip for securing suture, wherein the clip has a locked and an unlocked configuration, the clip comprising:
a generally tubular body comprising a distal end, a proximal end, an outer wall defining sides of the generally tubular body and extending generally from the distal end to the proximal end, a distal portion, and a proximal portion, wherein the generally tubular body has a length and is generally straight in the unlocked configuration and is bent in the locked configuration;
an inner lumen extending through the generally tubular body from the distal end to the proximal end;
a hinge point, wherein the distal portion extends from the distal end to the hinge point, and the proximal portion extends from the proximal portion to the hinge point, and the generally tubular body is configured, when in the locked configuration, to bend at the hinge point such that the distal portion is rotated about the hinge point with respect to the proximal portion;
a proximal tab cut from the outer wall of the generally tubular body at the proximal portion of the generally tubular body, wherein the proximal tab comprises a proximal tab base at which the proximal tab is secured to the outer wall, the proximal tab further comprising a proximal tab free end, wherein the proximal tab base and the proximal tab free end are on opposing ends of the proximal tab, and wherein the proximal tab free end is configured to extend, when in the locked configuration, into the inner lumen at the hinge point; and
a distal tab cut from the outer wall of the generally tubular body at the distal portion of the generally tubular body, wherein the distal tab comprises a distal tab base at which the distal tab is secured to the outer wall, the distal tab further comprising a distal tab free end, wherein the distal tab base and the distal tab free end are on opposing ends of the distal tab, and therein the distal tab free end is configured to extend, when in the locked configuration, into the inner lumen at the hinge point;
wherein the proximal tab and distal tab are cut from the same side of the generally tubular body.

13. The clip of claim 12, wherein the proximal tab free end is positioned distally of the proximal tab base.

14. The clip of claim 13, wherein the distal tab free end is positioned proximally of the distal tab base.

15. The clip of claim 14, wherein the proximal tab comprises a proximal tab outer surface, and the distal tab comprises a distal tab outer surface, and wherein when the clip is in the locked configuration the proximal tab outer surface engages against and contacts the distal tab outer surface.

16. The clip of claim 15, wherein the proximal tab free end and the distal tab free end are adjacent but separated by a break in the outer wall of the generally tubular body when the clip is in the open configuration.

17. The clip of claim 14, wherein the proximal tab and the distal tab engage against and contact each other when the clip is in the locked configuration.

18. The clip of claim 12, wherein the clip is biased toward the locked configuration.

* * * * *